US00PP28828P3

(12) United States Plant Patent
van den Haak

(10) Patent No.: US PP28,828 P3
(45) Date of Patent: Dec. 26, 2017

(54) ***HEUCHERA* PLANT NAMED 'CORALBERRY'**

(50) Latin Name: *Heuchera×hybrida*
Varietal Denomination: Coralberry

(71) Applicant: GOOTJES-ALLPLANT B.V., Schagen (NL)

(72) Inventor: Jelle van den Haak, Amsterdam (NL)

(73) Assignee: Gootjes-Allplant B.V., Schagen (NL)

( * ) Notice: Subject to any disclaimer, the term of this patent is extended or adjusted under 35 U.S.C. 154(b) by 41 days.

(21) Appl. No.: 14/998,592

(22) Filed: Jan. 23, 2016

(65) Prior Publication Data

US 2017/0215324 P1 Jul. 27, 2017

(51) Int. Cl.
*A01H 5/12* (2006.01)

(52) U.S. Cl.
USPC ..... Plt./440

(58) Field of Classification Search
USPC ..... Plt./440
CPC ... A01H 5/12; A01H 5/02; A01H 5/00; A01H 5/025
See application file for complete search history.

(56) References Cited

PUBLICATIONS

Visions Pictures & Photography *Heuchera* Indian Summer Coral Berry, retrieved on Apr. 25, 2017, retrieved from the Internet at <https://www.visionspictures.com/image/visi/visi141831> one page.*

* cited by examiner

*Primary Examiner* — June Hwu
(74) *Attorney, Agent, or Firm* — C. A. Whealy

(57) ABSTRACT

A new and distinct cultivar of *Heuchera* plant named 'Coralberry', characterized by its compact and uniformly mounded plant habit; densely foliated and bushy appearance; dark pink-colored leaves; and good garden performance.

2 Drawing Sheets

Botanical designation: *Heuchera×hybrida.*
Cultivar denomination: 'CORALBERRY'.

BACKGROUND OF THE INVENTION

The present invention relates to a new and distinct *Heuchera* plant of *Heuchera*, botanically known as *Heuchera×hybrida* and hereinafter referred to by the name 'Coralberry'.

The objective of the breeding program is to create new compact *Heuchera* plants with attractive leaf colors with good garden performance.

The new *Heuchera* plant originated from a cross-pollination in April, 2010 in Heerhugowaard, The Netherlands of *Heuchera×hybrida* 'Crimson Curls', disclosed in U.S. Plant Pat. No. 13,729, as the female, or seed, parent with a proprietary selection of *Heuchera×hybrida* identified as code number 083-09-C012, not patented, as the male, or pollen, parent. The new *Heuchera* plant was discovered and selected by the Inventor as a single flowering plant within the progeny of the stated cross-pollination in a controlled greenhouse environment in Heerhugowaard, The Netherlands in July, 2011.

Asexual reproduction of the new *Heuchera* plant by meristem culture in controlled laboratory and greenhouse environments in Andijk, The Netherlands since March, 2013 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Coralberry'. These characteristics in combination distinguish 'Coralberry' as a new and distinct *Heuchera* plant:

1. Compact and uniformly mounded plant habit.
2. Densely foliated and bushy appearance.
3. Dark pink-colored leaves.
4. Good garden performance.

Plants of the new *Heuchera* differ from plants of the female parent, 'Crimson Curls', in leaf color as plants of 'Crimson Curls' have dark purple brown and crimson-colored leaves. In addition, leaf margins of plants of the new *Heuchera* are not as undulate (curly) as leaf margins of 'Crimson Curls'.

Plants of the new *Heuchera* differ from plants of the male parent selection in leaf color as plants of the male parent selection have orangish peach-colored leaves.

Plants of the new *Heuchera* can be compared to plants of the *Heuchera×hybrida* 'Georgia Plum', disclosed in U.S. Plant Pat. No. 24,507. In side-by-side comparisons, plants of the new *Heuchera* differ primarily from plants of 'Georgia Plum' in the following characteristics:

1. Plants of the new *Heuchera* are more compact and denser than plants of 'Georgia Plum'.
2. Plants of the new *Heuchera* and 'Georgia Plum' differ in leaf color as plants of 'Georgia Plum' have purple pink-colored leaves.

BRIEF DESCRIPTION OF THE PHOTOGRAPHS

The accompanying colored photographs illustrates the overall appearance of the new *Heuchera* plant showing the colors as true as it is reasonably possible to obtain in colored reproductions of this type. Colors in the photograph may differ slightly from the color values cited in the detailed botanical description which accurately describe the colors of the new *Heuchera* plant.

The photograph on the first sheet is a side perspective view of a typical flowering plant of 'Coralberry' grown in a container.

The photograph at the top of the second sheet is a close-up view of a typical flowering plant of 'Coralberry'.

The photograph at the bottom of the second sheet is a close-up view of typical leaves of 'Coralberry'.

DETAILED BOTANICAL DESCRIPTION

The aforementioned photographs and following observations, measurements and values describe plants grown during the spring and early summer in 17-com containers in an outdoor nursery in Wieringerwerf, The Netherlands and under cultural practices typical of commercial *Heuchera* production. During the production of the plants, day temperatures ranged from 10° C. to 25° C. and night temperatures ranged from 4° C. to 15° C. Plants were 14 weeks old when the photographs and the description were taken. In the description, color references are made to The Royal Horticultural Society Colour Chart, 2007 Edition, except where general terms of ordinary dictionary significance are used.

Botanical classification: *Heuchera×hybrida* 'Coralberry'.

Parentage:

*Female, or seed, parent.*—*Heuchera×hybrida* 'Crimson Curls', disclosed in U.S. Plant Pat. No. 13,729.

*Male, or pollen, parent.*—Proprietary selection of *Heuchera×hybrida* identified as code number 083-09-C012, not patented.

Propagation:

*Type.*—By meristem culture.

*Time to initiate roots, summer.*—About ten days at temperatures about 22° C.

*Time to initiate roots, winter.*—About 15 days at temperatures about 20° C.

*Time to produce a rooted young plant, summer.*—About 42 days at temperatures about 20° C.

*Time to produce a rooted young plant, winter.*—About 50 days at temperatures about 20° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial; basal rosette plant habit with leaves developing from the base; densely foliated and dense and bushy appearance; compact and uniformly mounded plant habit; moderately vigorous growth habit.

*Plant height, soil level to top of foliar plane.*—About 24.5 cm.

*Plant height, soil level to top of inflorescences.*—About 43 cm.

*Plant diameter or spread.*—About 55.2 cm.

Leaf description:

*Quantity and arrangement.*—About eleven leaves per basal rosette; leaves, simple.

*Length.*—About 11.9 cm.

*Width.*—About 11.5 cm.

*Shape.*—Overall, broadly ovate to close to orbicular; palmately lobed.

*Apex.*—Short and abruptly acute.

*Base.*—Hastate, lobes slightly to moderately imbricate.

*Margin.*—Seven-lobed; crenate.

*Texture, upper surface.*—Pubescent.

*Texture, lower surface.*—Pubescent; pubescence more prominent along veins.

*Luster, upper surface.*—Matte.

*Luster, lower surface.*—Moderately glossy.

*Venation pattern.*—Palmate; reticulate.

*Color.*—Developing leaves, upper surface: Close to 183C; venation, close to N199B to N199C. Developing leaves, lower surface: Close to 187C; venation, close to 186A to 186B. Fully expanded leaves, upper surface: Close to between N77D and 183D; fading to closer to 182C; venation, close to N199B to N199C. Fully expanded leaves, lower surface: Close to 187B fading to closer to 187D; venation, close to 186A to 186B.

*Petioles.*—Length: About 19.5 cm. Diameter: About 3 mm. Texture, upper and lower surfaces: Densely pubescent. Color, upper and lower surfaces: Close to 187B.

Flower description:

*Flower type and flowering habit.*—Single campanulate flowers arranged on compound spikes; each spike with about 120 flowers; about 360 flowers develop per plant during the flowering season; flowers face mostly outward to slightly drooping.

*Fragrance.*—None detected.

*Time of flowering.*—Plants flower continuously from the late spring into the summer in The Netherlands.

*Inflorescence longevity.*—Individual flowers last about one week on the plant; flowers not persistent.

*Inflorescence length.*—About 43.5 cm.

*Inflorescence width.*—About 6.7 cm.

*Flower diameter.*—About 4 mm.

*Flower depth (height).*—About 6 mm.

*Flower buds.*—Height: About 3 mm. Diameter: About 2 mm. Shape: Elliptic. Color: Close to 61B.

*Petals.*—Quantity and arrangement: Five petals in a single whorl. Length: About 3 mm. Width: About 0.6 mm. Shape: Oblanceolate. Apex: Narrowly acute. Margin: Entire. Texture, upper and lower surfaces: Smooth, glabrous. Luster, upper and lower surfaces: Matte. Color: When opening, upper surface: Lighter than NN155D. When opening, lower surface: Close to NN155D slightly tinged with close to 62C to 62D. Fully opened, upper and lower surfaces: Lighter than NN155D.

*Sepals.*—Quantity and arrangement: Five sepals in a single whorl; fused at base. Length: About 4 mm. Width: About 1.5 mm. Shape: Roughly elliptic. Apex: Broadly acute. Margin: Entire. Texture, upper surface: Smooth. Texture lower surface: Densely pubescent. Color: When opening, upper surface: Close to between N155B and 69D; towards the apex, close to 145B. When opening, lower surface: Close to 62C; towards the base, close to 68B; towards the apex, close to N144D. Fully opened, upper surface: Close to between N155B and 69D; towards the apex, close to 145B. Fully opened, lower surface: Close to 62D; towards the base, close to 62C; towards the apex, close to N144D.

*Peduncles*.—Length, primary: About 43.1 cm. Length, lateral: About 0.3 cm to 3.2 cm. Diameter, primary: About 2.5 mm. Diameter, lateral: About 1 mm. Strength: Moderately strong. Aspect, primary: Mostly erect. Aspect, lateral: About 50° from primary peduncles. Texture: Pubescent. Color: Close to 187A to 187B.

*Pedicels*.—Length: About 2.5 mm. Diameter: About 0.5 mm. Strength: Moderately strong. Color: Close to 177A; distally, close to 156B.

*Reproductive organs*.—Androecium: Stamen number: Five per flower. Filament length: About 1.5 mm. Filament color: Close to NN155D. Anther length: About 0.5 mm. Anther shape: Deltoid. Anther color: Close to 10A. Amount of pollen: Scarce. Pollen color: Close to 16B. Gynoecium: Pistil number: Two per flower. Pistil length: About 3.5 mm. Stigma shape: Pointed. Stigma color: Close to N155B. Style length: About 3.25 mm. Style color: Close to between N155B and 62D; towards the base, close to 62D. Ovary color: Close to 62D.

*Seeds and fruits*.—Seed and fruit development have not been observed on plants of the new *Heuchera* to date.

Pathogen & pest resistance: Resistance to pathogens and pests has not been observed on plants of the new *Heuchera* grown under commercial conditions.

Garden performance: Plants of the new *Heuchera* have been observed to have good garden performance and to tolerate high temperatures about 35° C. and to be hardy to USDA Hardiness Zone 3.

It is claimed:

1. A new and distinct *Heuchera* plant named 'Coralberry' as illustrated and described.

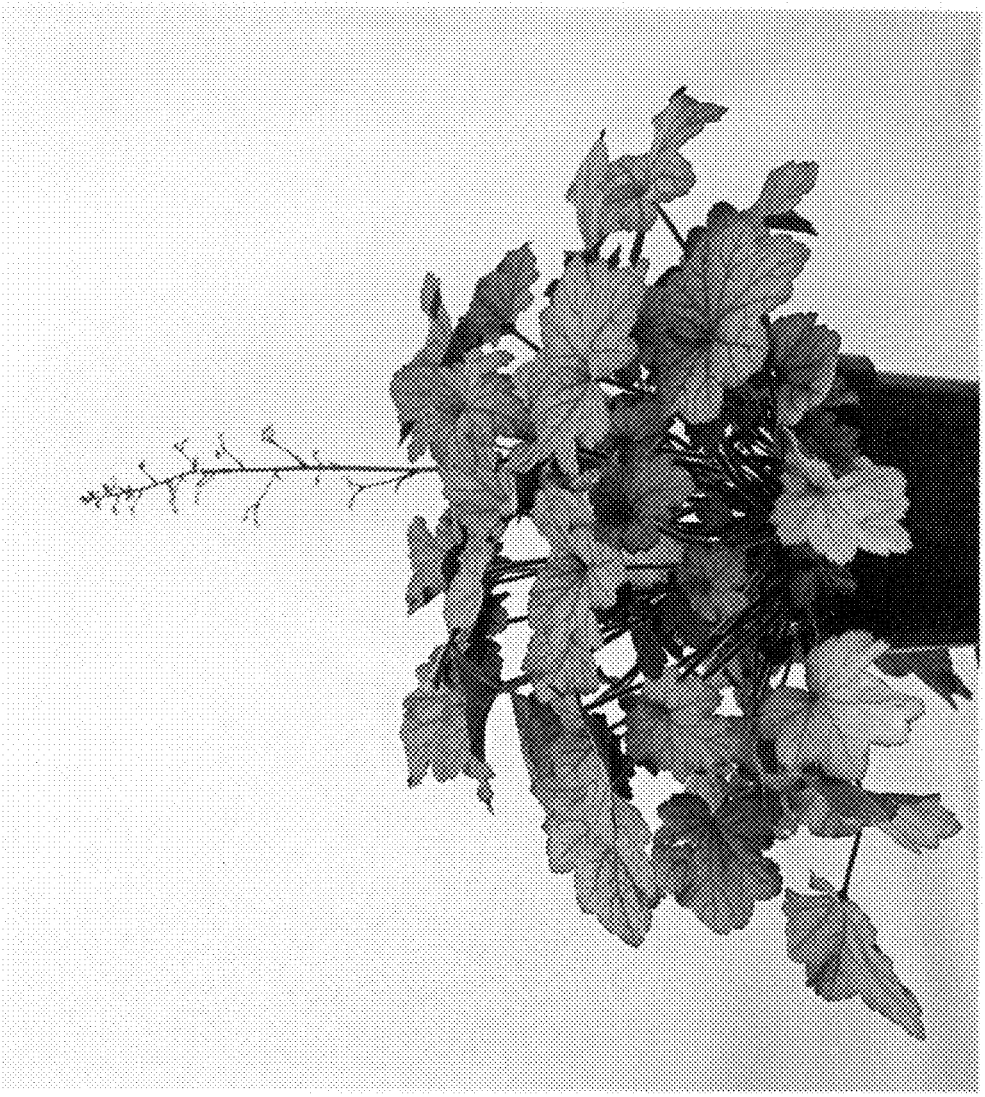

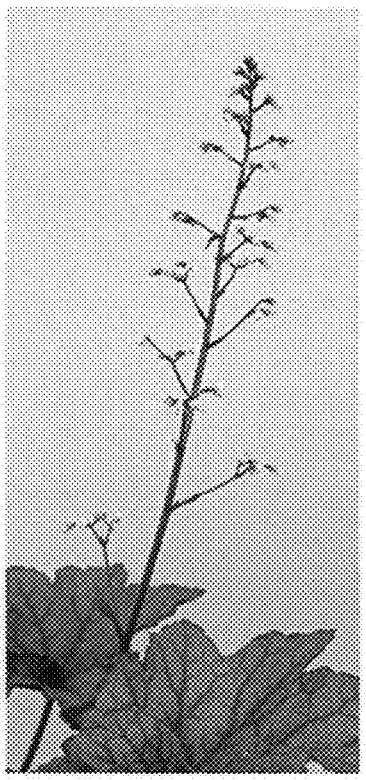
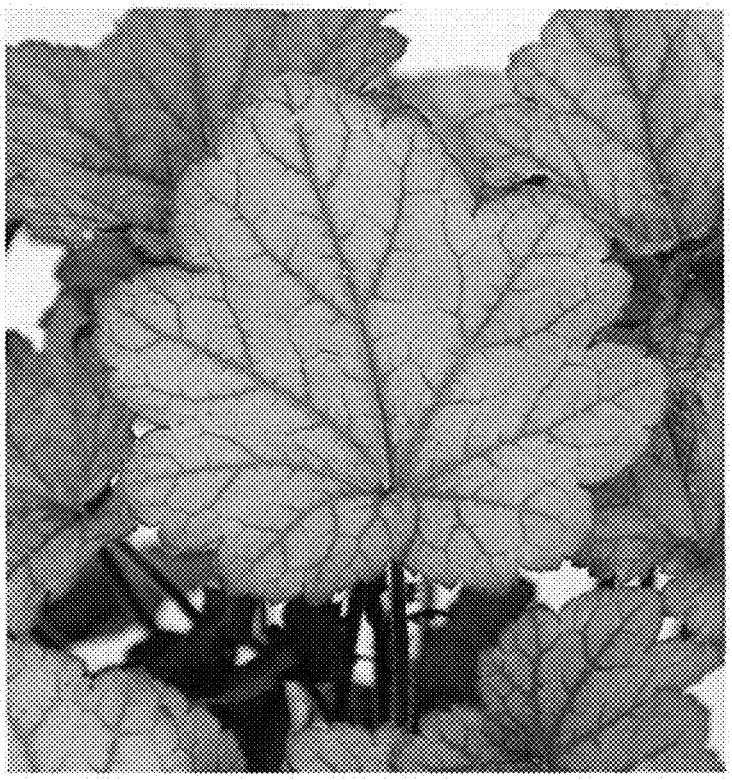

* * * * *